US011969265B2

(12) United States Patent
Koch et al.

(10) Patent No.: US 11,969,265 B2
(45) Date of Patent: Apr. 30, 2024

(54) NEURAL NETWORK CLASSIFICATION OF OSTEOLYSIS AND SYNOVITIS NEAR METAL IMPLANTS

(71) Applicants: THE MEDICAL COLLEGE OF WISCONSIN, INC., Milwaukee, WI (US); New York Society for the Relief of the Ruptured and Crippled, Maintaining the Hospital for Special Surgery, New York, NY (US)

(72) Inventors: Kevin M. Koch, Wauwatosa, WI (US); Andrew S. Nencka, Greendale, WI (US); Robin A. Karr, Wauwatosa, WI (US); Bradley J. Swearingen, Waukesha, WI (US); Hollis Potter, Greenwich, CT (US); Matthew F. Koff, Livingston, NJ (US)

(73) Assignees: The Medical College of Wisconsin, Inc., Milwaukee, WI (US); New York Society for the Relief of the Ruptured and Crippled, Maintaining the Hospital for Special Surgery, New York, NY (US)

( * ) Notice: Subject to any disclaimer, the term of this patent is extended or adjusted under 35 U.S.C. 154(b) by 756 days.

(21) Appl. No.: 16/975,910

(22) PCT Filed: Mar. 4, 2019

(86) PCT No.: PCT/US2019/020595
§ 371 (c)(1),
(2) Date: Aug. 26, 2020

(87) PCT Pub. No.: WO2019/169403
PCT Pub. Date: Sep. 6, 2019

(65) Prior Publication Data
US 2020/0410674 A1    Dec. 31, 2020

Related U.S. Application Data

(60) Provisional application No. 62/637,812, filed on Mar. 2, 2018.

(51) Int. Cl.
*A61B 5/00*         (2006.01)
*A61B 5/055*        (2006.01)
(Continued)

(52) U.S. Cl.
CPC ............ *A61B 5/7267* (2013.01); *A61B 5/055* (2013.01); *A61B 5/4504* (2013.01);
(Continued)

(58) Field of Classification Search
CPC ... A61B 5/7264; A61B 5/4528; A61B 5/7267; A61B 5/4504; A61B 5/4514;
(Continued)

(56) References Cited

U.S. PATENT DOCUMENTS 7,807,389 B2 * 10/2010 Ritchlin ........... G01N 33/56966
                                                        436/63
10,061,007 B2 * 8/2018 Gui ................. G01R 33/56536
(Continued)

FOREIGN PATENT DOCUMENTS

WO    WO-2008074151 A1 *  6/2008  ........... A61B 5/4528
WO    WO-2014113584 A1 *  7/2014  ........... A61K 31/192

OTHER PUBLICATIONS

J. Freyschmidt et al., Radiologe, 2016, 56:904-909.
(Continued)

*Primary Examiner* — John Villecco
*Assistant Examiner* — Courtney Joan Nelson
(74) *Attorney, Agent, or Firm* — Quarles & Brady LLP

(57) ABSTRACT

Systems and methods for training and implementing a machine learning algorithm to generate feature maps depict-
(Continued)

ing spatial patterns of features associated with osteolysis, synovitis, or both. MRI data, including multispectral imaging data, are input to the trained machine learning algorithm to generate the feature maps, which may indicate features such as a location and probability of a pathology classification, a severity of synovitis, a type of synovitis, a synovial membrane thickness, and other features associated with osteolysis or synovitis. In some implementations, synovial anatomy are segmented in the MRI data before inputting the MRI data to the machine learning algorithm. These segmented MRI data may be generated using another trained machine learning algorithm.

19 Claims, 8 Drawing Sheets

(51) Int. Cl.
| | | |
|---|---|---|
| *G06F 18/213* | (2023.01) | |
| *G06F 18/24* | (2023.01) | |
| *G06N 3/045* | (2023.01) | |
| *G06N 3/088* | (2023.01) | |
| *G06T 7/00* | (2017.01) | |
| *G06T 7/11* | (2017.01) | |
| *G16H 30/20* | (2018.01) | |
| *G16H 30/40* | (2018.01) | |
| *G16H 50/20* | (2018.01) | |
| *G16H 50/30* | (2018.01) | |
| *G16H 50/50* | (2018.01) | |
| *G16H 50/70* | (2018.01) | |

(52) U.S. Cl.
CPC .......... *A61B 5/4851* (2013.01); *G06F 18/213* (2023.01); *G06F 18/24* (2023.01); *G06N 3/045* (2023.01); *G06N 3/088* (2013.01); *G06T 7/0012* (2013.01); *G06T 7/11* (2017.01); *G16H 30/20* (2018.01); *G16H 30/40* (2018.01); *G16H 50/20* (2018.01); *G16H 50/30* (2018.01); *G16H 50/50* (2018.01); *G16H 50/70* (2018.01); *A61B 2576/02* (2013.01); *G06T 2207/10088* (2013.01); *G06T 2207/20081* (2013.01); *G06T 2207/20084* (2013.01); *G06T 2207/30008* (2013.01)

(58) Field of Classification Search
CPC ... A61B 5/4851; A61B 6/5217; A61B 8/5223; A61B 1/000096; A61B 2576/02; A61B 5/055; G06T 7/11; G06T 7/0012; G06T 2207/20081; G06T 2207/20084; G06T 2207/30008; G06T 2207/30012; G06T 7/00; G06T 2207/10088; G16H 50/20; G16H 30/40; G16H 30/20; G16H 50/30; G16H 50/00; G16H 70/60; G16H 50/50; G16H 50/70; G06N 20/00; G06N 3/045; G06N 3/088; G06N 3/08; G06F 18/24; G06F 18/213
See application file for complete search history.

(56) References Cited

U.S. PATENT DOCUMENTS

| | | | |
|---|---|---|---|
| 10,638,949 | B2 | 5/2020 | Koch |
| 2008/0139920 | A1* | 6/2008 | Biglieri .................. A61B 5/055 600/410 |
| 2009/0306496 | A1 | 12/2009 | Koo et al. |
| 2013/0137962 | A1* | 5/2013 | Urish .................. A61B 5/7264 600/410 |
| 2017/0200065 | A1* | 7/2017 | Wang .................. G06V 10/764 |
| 2017/0293009 | A1 | 10/2017 | Meade et al. |

OTHER PUBLICATIONS

M. Vahlensieck, Radiologe, 2006, 46:65-70.
Aram, P., et al. "Use of kernel-based Bayesian models to predict late osteolysis after hip replacement." Journal of The Royal Society Interface 10.88 (2013): 20130678.
Frid-Adar, M. et al. Synthetic data augmentation using GAN for improved liver lesion classification. In Biomedical Imaging (ISBI 2018), 2018 IEEE 15th International Symposium on, pp. 289-293. IEEE, 2018.
Gibson, E. et al. Niftynet: a deep-learning platform for medical imaging. Computer Methods and Programs in Biomedicine, 158:113-122, 2018.
Girshick, R. et al. Rich feature hierarchies for accurate object detection and semantic segmentation. In Proceedings of the IEEE conference on computer vision and pattern recognition, pp. 580-587, 2014.
Hauptfleisch, J. et al. A MRI classification of periprosthetic soft tissue masses (pseudotumours) associated with metal-on-metal resurfacing hip arthroplasty. Skeletal radiology, 41(2): 149-155, 2011.
Hayter, Cl et al. MRI After Arthroplasty: Comparison of MAVRIC and Conventional Fast Spin-Echo Techniques. American Journal of Roentgenology, 197(3):W405-W411, Sep. 2011.
He, K. et al. Mask r-cnn. In Computer Vision (ICCV), 2017 IEEE International Conference on, pp. 2980-2988. IEEE, 2017.
International Searching Authority. International Search Report and Written Opinion for application PCT/US2019/020595. dated May 23, 2019. 8 pages.
Karpathy, A. et al. Large-scale video classification with convolutional neural networks. In Proceedings of the IEEE conference on Computer Vision and Pattern Recognition, pp. 1725-1732, 2014.
Koff, M. et al. Clinical Feasibility of Isotropic MAVRIC SL Imaging of Total Joint Arthroplasties. Proceedings of the ISMRM, p. 0331, 2018.
Krizhevsky, A. et al. ImageNet Classification with Deep Convolutional Neural Networks. Advances in Neural Information Processing Systems 25 (2012).
Long, J. et al. Fully convolutional networks for semantic segmentation. In Proceedings of the IEEE Conference on Computer Vision and Pattern Recognition, pp. 3431-3440, 2015.
Maier, Cf et al. T2 quantitation of articular cartilage at 1.5 T. Journal of Magnetic Resonance Imaging, 17(3):358-364, 2003.
Nawabi, Dh et al. Magnetic Resonance Imaging Findings in Symptomatic Versus Asymptomatic Subjects Following Metal-on-Metal Hip Resurfacing Arthroplasty. J. Bone Joint Surg. Am., 95(10): 895-902, May 2013.
Nawabi, Dh et al. MRI Predicts ALVAL and Tissue Damage in Metal-on-Metal Hip Arthroplasty. Clinical Orthopaedics and Related Research R , 472(2):471-481, 2013.
Pedoia, V. et al. Fully automatic analysis of the knee articular cartilage T1p relaxation time using voxel-based relaxometry. Journal of Magnetic Resonance Imaging, 43(4):970-980, 2016.
Russakovsky, O. et al. ImageNet Large Scale Visual Recognition Challenge. International Journal of Computer Vision, 115(3):211-252, Apr. 2015.

* cited by examiner

NEURAL NETWORK CLASSIFICATION OF OSTEOLYSIS AND SYNOVITIS NEAR METAL IMPLANTS

CROSS-REFERENCE TO RELATED APPLICATIONS

This application is a national stage filing under 35 U.S.C. 371 of International Application No. PCT/US2019/020595, filed Mar. 4, 2019, which claims the benefit of U.S. Provisional Patent Application Ser. No. 62/637,812, filed on Mar. 2, 2018, and entitled "NEURAL NETWORK CLASSIFICATION OF OSTEOLYSIS AND SYNOVITIS NEAR METAL IMPLANTS," both of which are herein incorporated by reference in their entirety.

STATEMENT REGARDING FEDERALLY SPONSORED RESEARCH

This invention was made with government support under AR064840 awarded by the National Instituted of Health. The government has certain rights in the invention.

BACKGROUND

An estimated 2.5 million Americans currently have artificial hip joints, or hip arthroplasty ("HA"), all of which have inevitable failure modes that depend heavily on patient-specific risk and genetic factors. In practice, most HA failures requiring revision are due to alterations in adjoining tissues (e.g., bone, synovium, muscle). These tissue alterations are best assessed using magnetic resonance imaging ("MRI"). In particular, MRI can visualize implant loosening, periprosthetic bone loss, and adverse host-mediated synovial reactions, thus providing substantial value to surgeons. This added value comes in the form of improved and earlier diagnoses of disease progression in cases of symptomatic HA.

MRI acquisitions that utilize three-dimensional multispectral imaging ("3D-MSI") technology can resolve the historic metal artifact challenges of imaging near HA and have expanded the potential clinical role of MRI in HA management. However, the mitigation of the physical challenge of MRI metal artifacts has exposed another challenge: the complexity of MRI interpretation in the immediate vicinity of HA. A variety of image signatures, spanning from synovial abnormalities, tissue reactions, and osteolysis are often readily identifiable near symptomatic or asymptomatic HA on 3D-MSI MRI, but require a fairly steep learning curve on the part of the interpreting radiologist or clinician. This challenge, combined with the complex manifestation of the MRI findings, results in poor characterization of these clinically relevant MRI signatures and an under-utilization of the imaging technology in many clinical orthopedic imaging environments. This under-utilization of available imaging technology is particularly relevant in imaging departments that are not solely focused on orthopedics.

SUMMARY OF THE DISCLOSURE

The present disclosure addresses the aforementioned drawbacks by providing a method for generating a feature map that depicts a spatial distribution or pattern of a feature associated with osteolysis or synovitis. Magnetic resonance imaging (MRI) data acquired from a subject are accessed by a computer system. A trained machine learning algorithm that has been trained on training data to generate feature maps associated with at least one of osteolysis or synovitis is also accessed by the computer system. The MRI data are input to the trained machine learning algorithm in order to generate output with the computer system. The generated output includes at least one feature map that depicts a spatial distribution of a feature associated with at least one of osteolysis or synovitis.

It is another aspect of the present disclosure to provide a method for constructing and implementing a machine learning algorithm to a feature map that depicts spatial patterns of a feature associated with osteolysis or synovitis across a region in a subject. A trained machine learning algorithm can be generated by accessing training data with a computer system and training the machine learning algorithm based on the training data. The machine learning algorithm is trained on the training data to generate a feature map indicating a spatial pattern of the feature across a region-of-interest. The training data can include magnetic resonance imaging (MRI) data acquired from a plurality of subjects, and labeled data indicating a feature associated with at least one of osteolysis or synovitis for each of the plurality of subjects. A feature map that depicts a spatial pattern of the feature associated with at least one of osteolysis or synovitis is generated by inputting magnetic resonance images acquired from the subject to the trained machine learning algorithm.

It is another aspect of the present disclosure to provide a method for generating feature data that indicates a thickness of a synovial membrane in a subject. The method includes accessing with a computer system, magnetic resonance imaging (MRI) data acquired from a subject. A trained machine learning algorithm that has been trained on training data to generate feature data that indicates a thickness of a synovial membrane is also accessed by the computer system. The MRI data are input to the trained machine learning algorithm in order to generate output with the computer system. The output includes feature data that indicates a thickness of a synovial membrane in the subject.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here are systems and methods for utilizing a machine learning algorithm implemented with a hardware processor and memory to provide image-based deep learning on 3D-MSI MRI to provide supplementary guidance for radiological identification of common soft-tissue pathologies near HA or other metallic implants or objects. In particular, preliminary data demonstrates the promising capabilities of convolutional neural networks ("CNNs") trained on a cohort of normal and pathological 3D-MSI of HA (or patients with or other metallic implants or objects) to spatially identify periprosthetic bone loss (i.e., osteolysis) and adverse synovial responses. Using this artificial intelligence ("AI") analysis engine, feature maps advising potential soft tissue and bone pathology can be constructed on a subject-specific basis and presented to radiologists and surgeons as a direct visual presentation of regional tissue abnormalities near HA or other metallic implants or objects. This computer-aided diagnosis ("CAD") approach can also serve to accelerate and broaden the adoption of advanced MRI utility in HA management by adding simplicity and intuition to application workflows.

In addition, the systems and methods described in the present disclosure could aid in the education and intuitive comprehension of tissue signatures near HA or other metallic implants or objects in large patient cohorts, allowing for the generation of important natural history datasets.

The systems and methods described in the present disclosure can also enable image-based soft-tissue pathology differentiation near hip replacements or other metallic implants or objects. Such technology can offer quantitative evidence informing the severity of tissue disease in failing hip replacements (or other joint replacements or metallic orthopedic implants) and better evaluate the necessity and mechanisms for revision procedures.

It is one aspect of the present disclosure to provide a deep learning classification model for spatially highlighting osteolysis and synovitis on 3D-MSI MRI. As one example, supervised model training can utilize a neural network classification infrastructure. The output of the neural network will be 3D synovitis and osteolysis feature maps for individual subjects. The scale on the feature maps will represent the local probability for a given pathological classification. The performance of the network model can be statistically assessed (e.g., on a pixel-wise basis) against expert radiologist image annotations.

Figure 1:
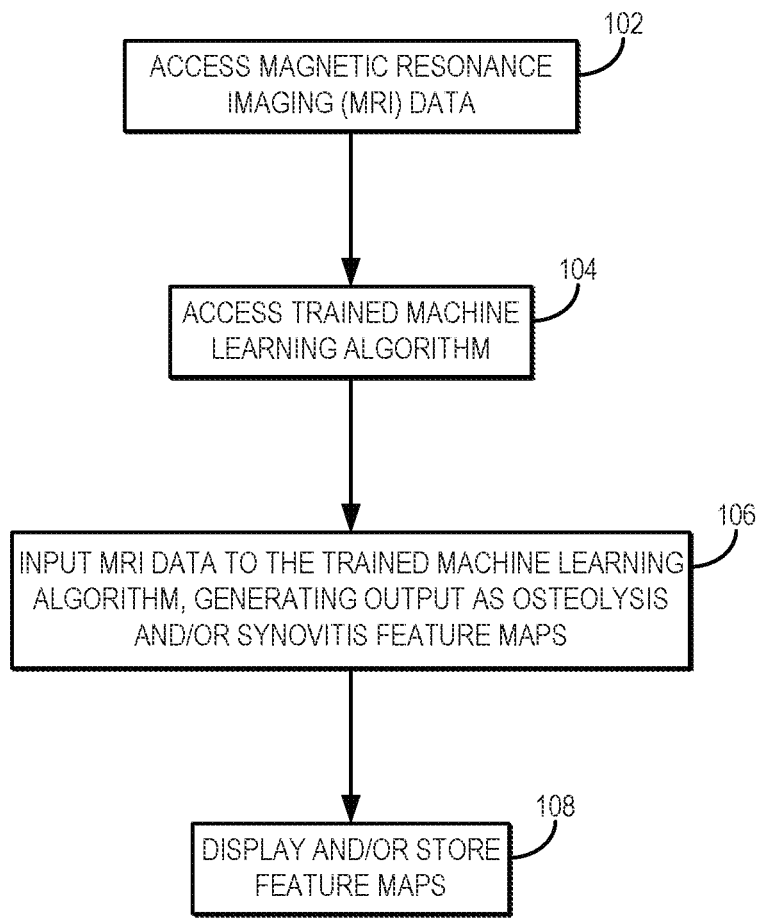
FIG. 1 is a flowchart setting forth the steps of an example method for generating a feature map that depicts spatial patterns of a feature associated with osteolysis and/or synovitis by inputting MRI data into a trained machine learning algorithm.

Referring now to FIG. 1, a flowchart is illustrated as setting forth the steps of an example method for generating feature maps associated with osteolysis, synovitis, or both, using a trained machine learning algorithm that has been trained on relevant training data to generate these feature maps.

The method includes accessing magnetic resonance imaging ("MRI") data with a computer system, as indicated at step 102. The MRI data may include magnetic resonance signal data (e.g., k-space data), images reconstructed from k-space data, or parametric images or maps generated from magnetic resonance signal data, reconstructed images, or both. In some instances, the MRI data may also include texture feature maps generated from the magnetic resonance signal data, reconstructed images, or parametric images or maps. Texture features can include first-order statistics, second-order statistics, and other texture features known to those skilled in the art. The MRI data can be accessed by retrieving such data from a memory or other data storage device or medium. In other instances, the magnetic resonance data can be accessed by acquiring such data from a subject using an MRI system and communicating that data to the computer system.

As one example, the MRI data may include proton density-weighted images acquired with an MRI system. In other instances, however, the MRI data can include T1-weighted images, T2-weighted images, or other magnetic resonance images acquired using a desired pulse sequence to elicit the desired magnetic resonance imaging contrast. In general, the MRI data will include MSI data, which may include 2D-MSI data or 3D-MSI data, acquired using a multi-spectral imaging technique. In some examples, the MRI data may also include parametric maps indicating frequency information derived from the multi-spectral imaging (e.g., frequency bins, frequency offsets).

A trained machine learning algorithm is then accessed with the computer system, as indicated at step 104. Accessing the trained machine learning algorithm may include, for instance, accessing weights, biases, or both, which have been computed or otherwise estimated by training the machine learning algorithm on training data. When the machine learning algorithm implements a neural network, accessing the trained machine learning algorithm may include retrieving or otherwise accessing the particular neural network architecture to be implemented. For instance, data pertaining to the layers in the neural network architecture (e.g., number of layers, type of layers, ordering of layers, connections between layers) may be retrieved or otherwise accessed.

In some instances, more than one trained machine learning algorithm may be accessed. For example, a first machine learning algorithm may have been trained on first training data to generate a first feature map and a second machine learning algorithm may have been trained on second training data to generate a second feature map that is different from the first feature map. As an example, the first feature map may be associated with osteolysis whereas the second feature map may be associated with synovitis.

The MRI data are then input to the one or more trained machine learning algorithms, as indicated at step 106 in order to generate output as feature maps associated with osteolysis, synovitis, or both. Inputting the MRI data may include inputting data from the entire field-of-view represented in the MRI data, or may include inputting data from one or more regions-of-interest ("ROIs") that have been identified in the MRI data. As mentioned, the feature maps may depict the spatial distribution or spatial patterns of features, statistics, or other parameters associated with osteolysis, synovitis, or both.

As one example, the feature maps may indicate the local probability for a given pathological classification. For instance, the feature maps may indicate the location and/or probability of each pathology. Clinically, these feature maps can be used to give radiologists a baseline off which to diagnosis. Using the systems and methods described in the present disclosure, diagnosis of both osteolysis and synovitis could be done around other implants as well.

As another example, the feature maps may indicate the type of synovitis, not just the presence or absence of synovitis. For instance, the trained machine learning algorithms may be trained to implement automatic pattern recognition to generate feature maps that classify synovitis patterns on MRI data, such as 3D-MSI data. While synovial thickness and volumetric expansion can provide useful and established quantitative metrics of synovial health, they do not necessarily specify the nature or type of the synovial reaction. Using the systems and methods described in the present disclosure, the location, type, and severity of synovitis can be estimated in the generated feature maps. Robust monitoring of a soft tissue response may benefit from the ability to track changes of synovitis based on these feature maps.

In these instances, the one or more trained machine learning algorithms are trained and implemented to classify the severity and type of synovitis. Training of these machine learning algorithms can be performed using training data that include labeled data indicating segmented and classified regions of intermediate-to-severe synovitis. These labeled data may include manually segmented and classified regions that has been performed by a radiologist. Using machine learning algorithms that have been trained to classify and localize synovitis can provide advantages for generalized usage in HA assessment and can also be used an education tool for radiologists interpreting MRI near HA.

As still another example, the output of the trained machine learning algorithm may include feature data that indicates a thickness of the synovial membrane. In these instances the trained machine learning algorithm may include an encoding path of an encoder-decoder neural network that is implemented to provide a classifier (e.g., an 8-bit precision classifier) for maximal synovial thickness. In such examples, the feature data may be displayed to a user, such as on a graphical user interface. The feature data may be displayed, for instance, by displaying the feature data as an overlay on the MRI data, or may be displayed as a separate display element adjacent MRI data in a graphical user interface. The feature data may also be output in a report, which may include textual or numerical information or data.

As a non-limiting example, the systems and methods described in the present disclosure can be implemented to provide a voxel-wise synovitis classifier. Synovial segmentation can be used to focus this pattern detection network within regions of synovium or synovial expansion. In these instances, the network can be expanded to utilize the synovial mask as a secondary input to the training and inference phases. As one non-limiting example this may include implementing a region-based CNN (e.g., Mask R-CNN) network architecture to detect a bounding box of synovial area and then perform a voxel-wise synovitis identification only inside the synovial bounding box.

In some other implementations, the encoding path of an encoder-decoder neural network can be implemented to provide classification of identified synovitis regions based on synovitis type labels defined by radiologists during data curation.

These feature maps may then be displayed to a user, stored for later use or further processing, or both, as indicated at step 108.

Figure 2:
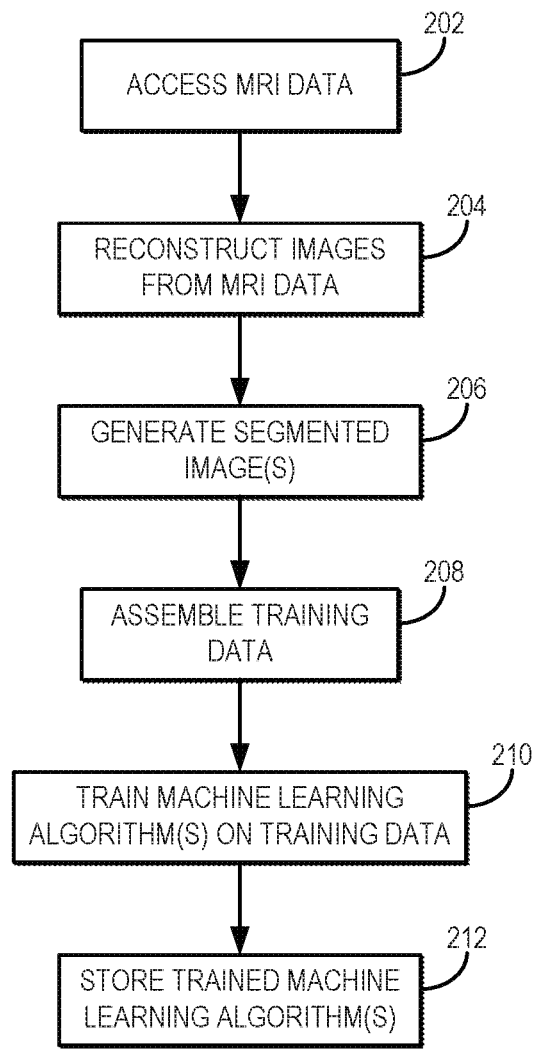
FIG. 2 is a flowchart setting forth the steps of an example method for training a machine learning algorithm to generate feature maps that depict spatial patterns of a feature associated with osteolysis and/or synovitis.

Referring now to FIG. 2, a flowchart is illustrated as setting forth the steps of an example method for training one or more machine learning algorithms on training data, such that the one or more machine learning algorithms are trained to receive input as MRI data in order to generate output as feature maps associated with osteolysis and/or synovitis.

The method includes accessing MRI data that have been acquired with an MRI system, as indicated at step 202. As described above, the MRI data may include magnetic resonance signal data (e.g., k-space data), images reconstructed from k-space data, or parametric images or maps generated from magnetic resonance signal data, reconstructed images, or both. The MRI data may also include texture feature maps. The MRI data can be accessed by retrieving such data from a memory or other data storage device or medium. In other instances, the magnetic resonance data can be accessed by acquiring such data from one or more subjects using an MRI system and communicating that data to the computer system.

When the MRI data includes magnetic resonance signal data, images can be reconstructed from the magnetic resonance signal data, as indicated at step 204. Segmented MRI data are then generated at step 206 by segmenting magnetic resonance images reconstructed from, or otherwise included in, the MRI data. The segmented MRI data can be generated by manually, semi-automatically, or automatically segmenting images. In some instances, the segmented MRI data can be generated by inputting MRI data to one or more trained machine learning algorithms that have been trained to generate output as segmented MRI data. For instance, the trained machine learning algorithms can be trained to generate output as segmented MRI data in which synovium has been segmented. These segmented MRI data may, therefore, include segmented synovium information that can be used as a restricted mask for synovial classification.

Training data are assembled next, as indicated at step 208. Assembling the training data may include assembling MRI data, segmented MRI data, and other relevant data. For instance, assembling the training data may include generating labeled data and including the labeled data in the training data. Labeled data may include MRI data, segmented MRI data, or other relevant data that have been labeled as belong to, or otherwise being associated with, one or more different classifications or categories. For instance, labeled data may include MRI data and/or segmented MRI data that have been labeled based on a probability of a pathological classification (e.g., osteolysis, synovitis, or both). The labeled data may include labeling all data within a field-of-view of the MRI data or the segmented MRI data, or may include labeling only those data in one or more ROIs in the MRI data and/or segmented MRI data. The labeled data may include data that are classified on a voxel-by-voxel basis, or a regional or larger volume basis.

One or more machine learning algorithms are trained on the training data, as indicated at step 210. The machine learning algorithm can be any suitable machine learning algorithm, and in some instances includes a machine learning algorithm based on a neural network. The neural network may be a convolutional neural network, and in some instances may include an encoder-decoder neural network, such as an encoder-decoder neural network that implements a U-Net architecture.

The one or more trained machine learning algorithms are then stored for later use, as indicated at step 212. Storing the machine learning algorithms may include storing weights, biases, or both, which have been computed or otherwise estimated by training the machine learning algorithm on the training data. When the machine learning algorithm implements a neural network, storing the trained machine learning algorithm may include storing the particular neural network architecture to be implemented. For instance, data pertaining to the layers in the neural network architecture (e.g., number of layers, type of layers, ordering of layers, connections between layers) may be stored.

Figure 3:
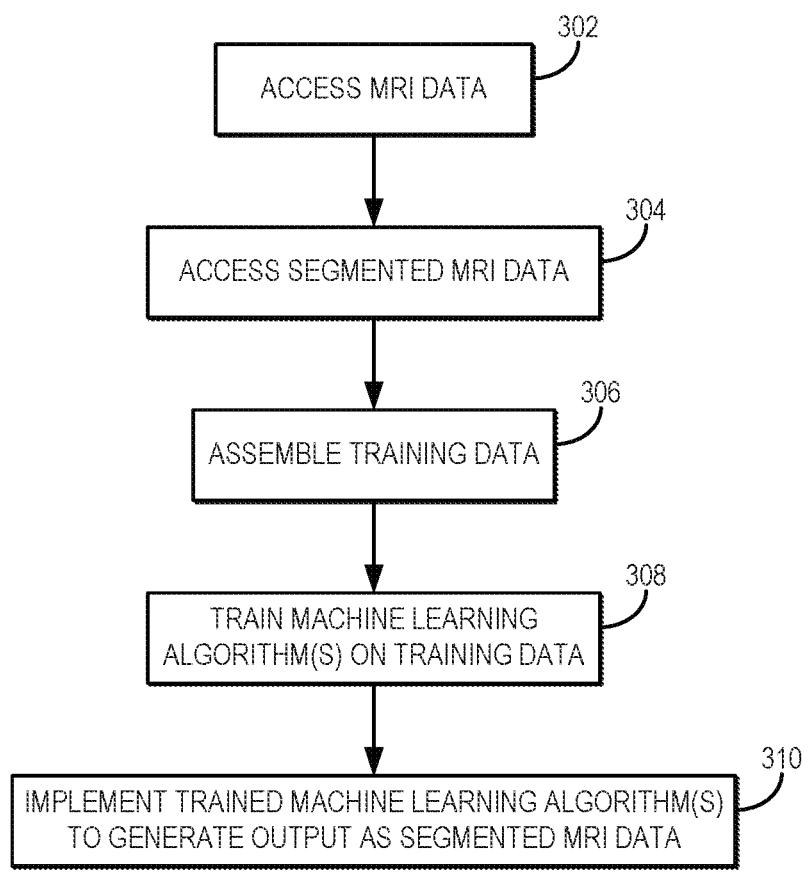
FIG. 3 is a flowchart setting forth the steps of an example method for training a machine learning algorithm to generate segmented MRI data that depict synovial anatomy that has been segmented in MRI data.

Referring now to FIG. 3, a flowchart is illustrated as setting forth the steps of an example method for training and implementing a machine learning algorithm for synovial segmentation and classification.

The method includes accessing MRI data, as indicated at step 302. As described above, the MRI data may include magnetic resonance signal data (e.g., k-space data), images reconstructed from k-space data, or parametric images or maps generated from magnetic resonance signal data, reconstructed images, or both. The MRI data may also include texture feature maps. The MRI data can be accessed by retrieving such data from a memory or other data storage device or medium. In other instances, the magnetic resonance data can be accessed by acquiring such data from one or more subjects using an MRI system and communicating that data to the computer system. As an example, the MRI data may include data or images acquired using an isotropic intermediate weighted 3D-MSI acquisition.

Segmented MRI data are then generated or otherwise accessed, as indicated at step 304. For instance, the segmented MRI data may include previously manually segmented datasets from 3D-MSI. The segmented MRI data may include images in which the synovium (e.g., the synovial envelope) have been manually segmented.

Training data are assembled at step 306. Assembling the training data may include, for example, assembling the MRI data and the corresponding segmented MRI data, on which the machine learning algorithm is to be trained. This step may include assembling the data into an appropriate data structure on which the machine learning algorithm can be trained.

One or more machine learning algorithms are trained on the training data, as indicated at step 308. The machine learning algorithm can be any suitable machine learning algorithm, and in some instances includes a machine learning algorithm based on a neural network. The neural network may be a convolutional neural network, and in some instances may include an encoder-decoder neural network, such as an encoder-decoder neural network that implements a U-Net architecture. In general, the same neural network architecture utilized for the osteolysis/synovitis feature map generation can also be used to generate a trained machine learning algorithm for synovial segmentation.

At step 310, the one or more trained machine learning algorithms can then be implemented to generated segmented MRI data by inputting MRI data acquired from a different subject into the trained machine learning algorithm, generating output as segmented MRI data in which synovial anatomy has been segmented. When applied to MRI data, the resulting synovial segmentation predictions can be used to compute synovial volumes in an unsupervised fashion. Such automated synovial health characterization is advantageous for generating feature maps of osteolysis and/or synovitis.

In other instances, the trained machine learning algorithms can be stored for later use. Storing the machine learning algorithms may include storing weights, biases, or both, which have been computed or otherwise estimated by training the machine learning algorithm on the training data. When the machine learning algorithm implements a neural network, storing the trained machine learning algorithm may include storing the particular neural network architecture to be implemented. For instance, data pertaining to the layers in the neural network architecture (e.g., number of layers, type of layers, ordering of layers, connections between layers) may be stored.

Similar to the methods described above for the synovial volume segmentation, a machine learning algorithm can also be trained as a synovial thickness classifier model. In these implementations, the training data can include maximal synovial thickness measurements estimated or otherwise made from the accessed MRI data. In some implementations, scalar thickness measurements can be converted into an 8-bit classifier table (256 levels) to reduce the dynamic range of the final rectifier filter within the neural network. The encoding path of an encoder-decoder neural network, such as those described in the present disclosure, can be utilized to train the thickness classifier.

As noted, the machine learning algorithm can include a neural network, such as a convolutional neural network, or other suitable machine learning algorithm, such as support vector machines ("SVM") and other algorithms based on supervised learning, unsupervised learning, deep learning, ensemble learning, dimensionality reduction, and so on.

Figure 4:
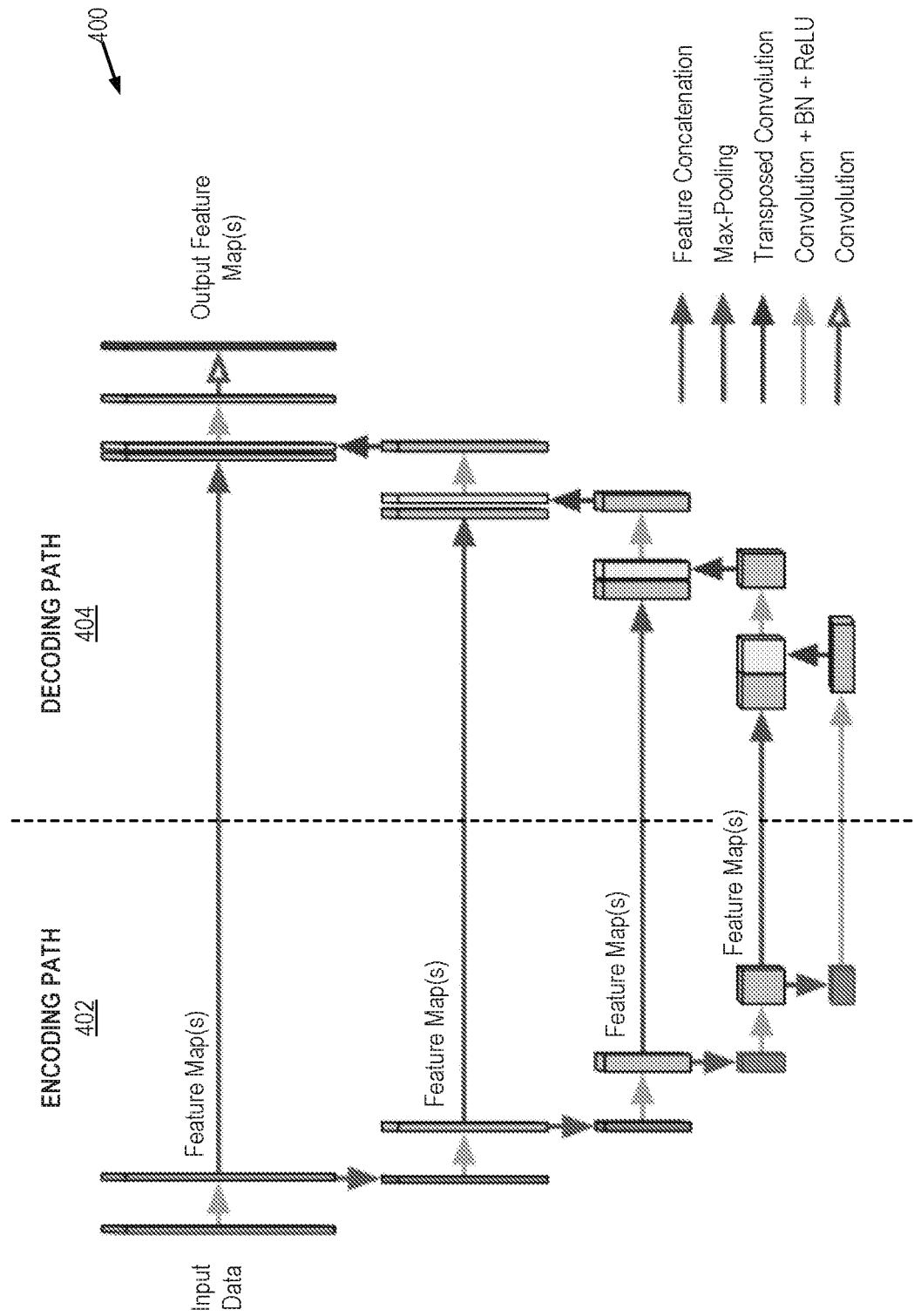
FIG. 4 is an example of an encoder-decoder neural network architecture that can be trained to generate feature maps, such as those described in the present disclosure.

As noted above, in some instances the trained neural network can be an encoder-decoder neural network, such as a three-dimensional encoder-decoder deep neural network. An example of such a neural network is shown in FIG. 4. The data input to the network 400 are the local field shift maps and the data output are estimates of the source magnetic susceptibility tensor at each input voxel. In this example, the applied encoder-decoder network architecture utilizes skip connections between the encoding path 402 and decoding path 404, which can effectively transfer local feature information from the encoding path to the decoding path and facilitate faster training.

The encoding path 402 generally implements a convolutional neural network. For instance, the encoding path 402 can include repeated application of convolutional layers (e.g., 3×3×3 convolutions) each followed by a batch normalization layer and a nonlinear layer, which may be a recitified linear unit ("ReLU"). The output of each convolutional layer is a feature map that is passed to the nonlinear layer. Each feature map generally represents a particular feature extracted at all locations on the input. Each nonlinear layer is followed by a downsampling layer, which may be a pooling layer, such as a max pooling layer (e.g., a max pooling layer using stride 2×2×2), an average pooling layer, an L2-norm pooling layer, or so on. The output of each nonlinear layer is a feature map that is passed to the downsampling layer. At each downsampling step, the number of feature channels in the feature map can be doubled, or otherwise increased.

The decoding path 404 generally includes a transposed convolutional layer with additional feature concatenation layers from the encoding layers. The output of each transposed convolutional layer is a feature map that is passed to the concatenation layer. At each transposed convolution step, the number of feature channels in the feature map can be halved, or otherwise reduced. As noted, each upsampled feature map is also concatenated with the corresponding feature map from the encoding path 402. The concatenated feature map is then passed to a convolutional layer followed by a batch normalization layer and a nonlinear layer (e.g., a ReLU). The output of the convolutional layer is a feature map that is passed to the batch normalization layer, the output of which is a feature map passed to the nonlinear layer. The final layer is a convolutional layer (e.g., a 1×1×1 convolution) with linear activation, which is applied to output the susceptibility estimations.

Figure 5:
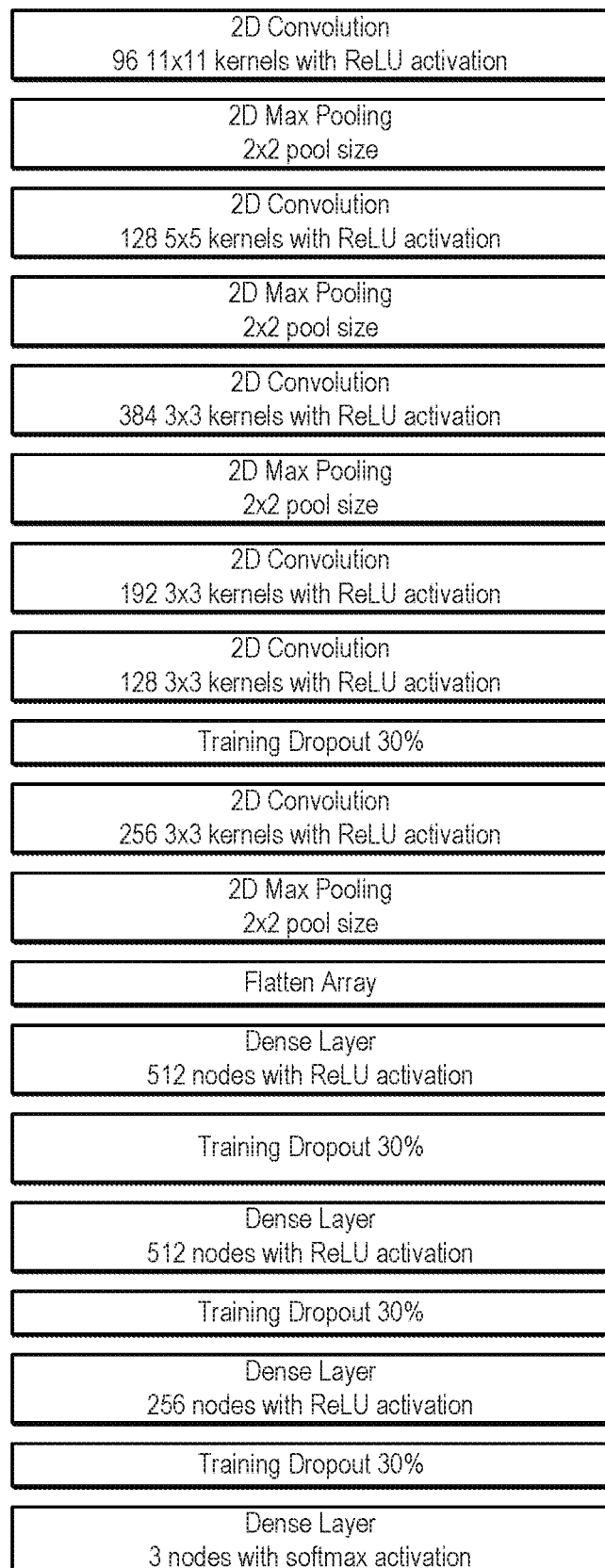
FIG. 5 is an example of another convolutional neural network that can be implemented to classify MRI data according to the methods described in the present disclosure.

In other instances, the neural network architecture shown in FIG. 5 can be used. Changes to the structure included a smaller image size, additional layers, and other minor parameter updates.

As one non-limiting example of an encoder-decoder neural network architecture that was implemented in an example study, each encoder step included two 3×3, 2D convolution layers followed by a single 2×2 max-pooling layer. Decoder steps had a single 2×2 up convolution followed by two 3×3, 2D convolution layers. The final layer was a single 1×1, 2D convolution which created a feature map of the same size as the input images. The model in this example had a depth of four, meaning there were a total of three max-pooling and up-sampling steps.

In this example, for each epoch, the input data were divided into batches of four, and a random distortion was applied to fifty percent of the data. Iterative performance was calculated using a binary cross entropy loss function for 200 epochs. Analysis of the trained model was performed on a voxel-wise basis. Synovitis prediction values were computed across entire slices for both the training, validation, and control testing image sets. Examination of a control testing cohort was performed by identifying slices in which a false positive high thresholded prediction region was found in an area of potential synovitis.

Figure 6:
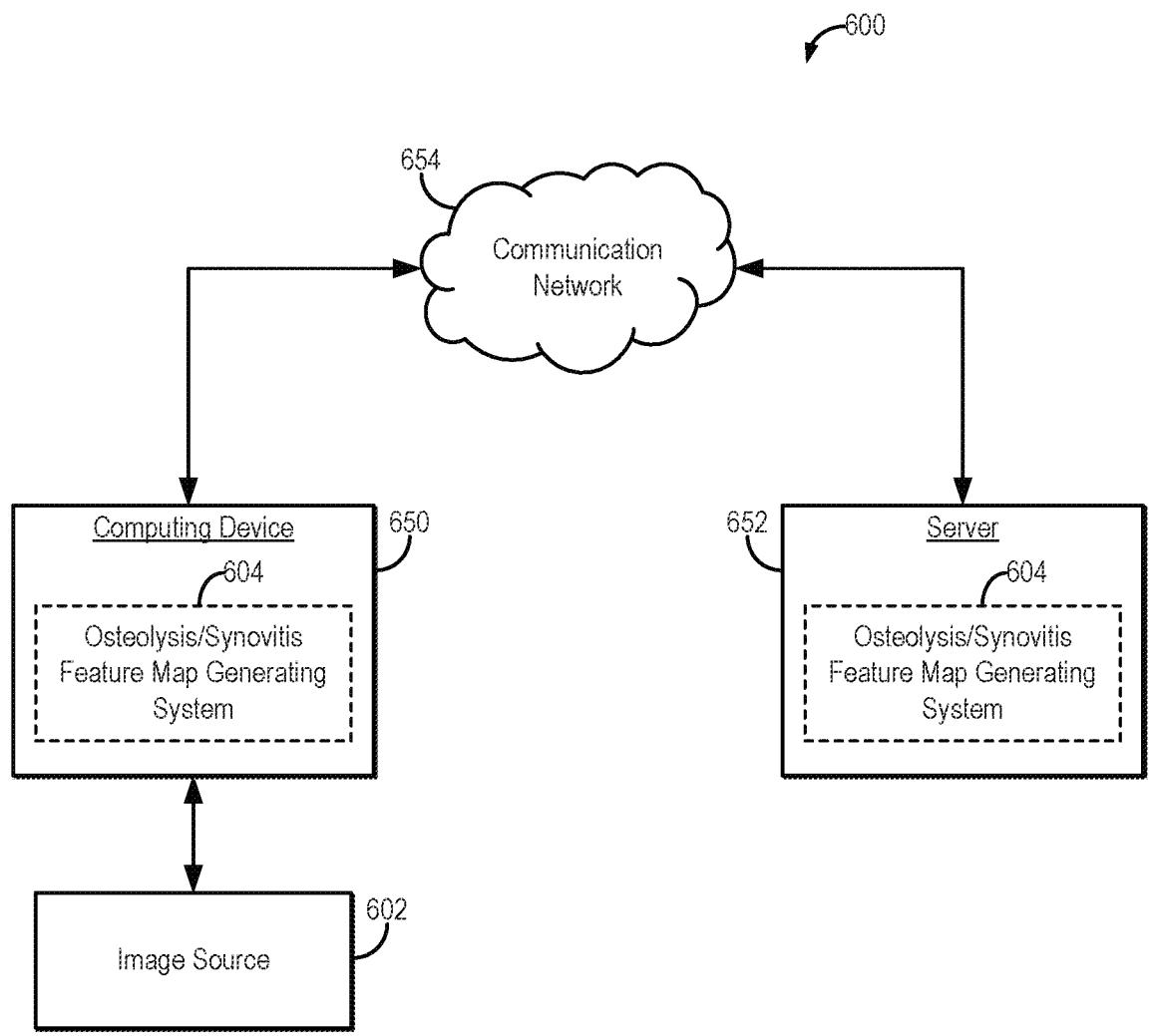
FIG. 6 is a block diagram of an example osteolysis/synovitis feature generating system for generating feature maps associated with osteolysis, synovitis, or both.

Referring now to FIG. 6, an example of a system 600 for generating feature maps indicative of osteolysis, synovitis, or both, in accordance with some embodiments of the systems and methods described in the present disclosure is shown. As shown in FIG. 6, a computing device 650 can receive one or more types of data (e.g., MRI data, segmented MRI data, training data) from image source 602, which may be a magnetic resonance image source. In some embodiments, computing device 650 can execute at least a portion of an osteolysis/synovitis feature map generating system 604 to generate feature maps that indicate the spatial distribution or spatial patterns of features, statistics, probabilities, estimates, or parameters associated with osteolysis and/or synovitis, these feature maps being generated from data received from the image source 602.

Additionally or alternatively, in some embodiments, the computing device 650 can communicate information about data received from the image source 602 to a server 652 over a communication network 654, which can execute at least a portion of the osteolysis/synovitis feature map generating system 604. In such embodiments, the server 652 can return information to the computing device 650 (and/or any other suitable computing device) indicative of an output of the osteolysis/synovitis feature map generating system 604.

In some embodiments, computing device 650 and/or server 652 can be any suitable computing device or combination of devices, such as a desktop computer, a laptop computer, a smartphone, a tablet computer, a wearable computer, a server computer, a virtual machine being executed by a physical computing device, and so on. The computing device 650 and/or server 652 can also reconstruct images from the data.

In some embodiments, image source 602 can be any suitable source of image data (e.g., measurement data, images reconstructed from measurement data), such as an MRI system, another computing device (e.g., a server storing image data), and so on. In some embodiments, image source 602 can be local to computing device 650. For example, image source 602 can be incorporated with computing device 650 (e.g., computing device 650 can be configured as part of a device for capturing, scanning, and/or storing images). As another example, image source 602 can be connected to computing device 650 by a cable, a direct wireless link, and so on. Additionally or alternatively, in some embodiments, image source 602 can be located locally and/or remotely from computing device 650, and can communicate data to computing device 650 (and/or server 652) via a communication network (e.g., communication network 654).

In some embodiments, communication network 654 can be any suitable communication network or combination of communication networks. For example, communication network 654 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 108 can be a local area network, a wide area network, a public network (e.g., the Internet), a private or semi-private network (e.g., a corporate or university intranet), any other suitable type of network, or any suitable combination of networks. Communications links shown in FIG. 6 can each be any suitable communications link or combination of communications links, such as wired links, fiber optic links, Wi-Fi links, Bluetooth links, cellular links, and so on.

Figure 7:
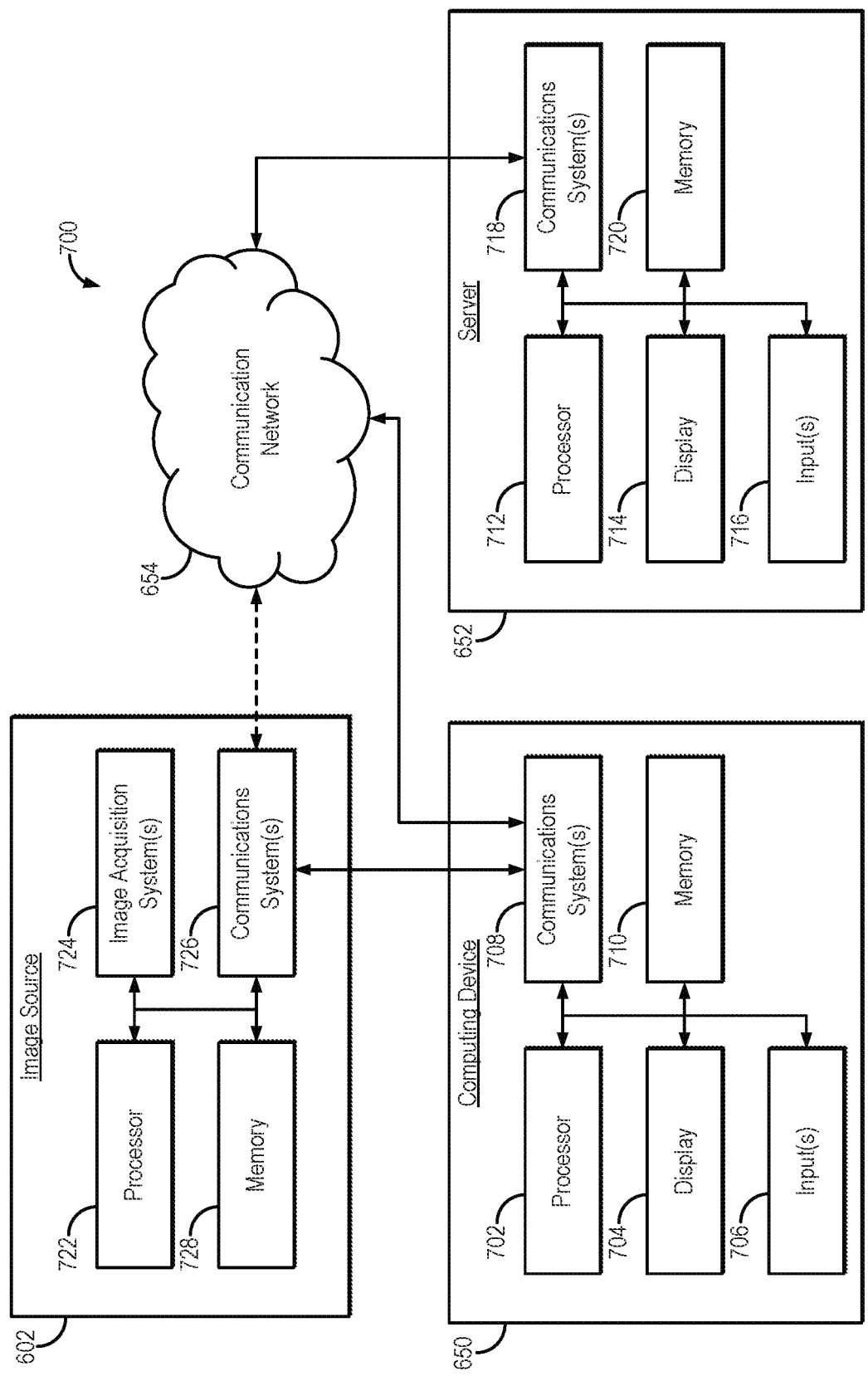
FIG. 7 is a block diagram of example hardware components that can implement the system of FIG. 6.

Referring now to FIG. 7, an example of hardware 700 that can be used to implement image source 602, computing device 650, and server 654 in accordance with some embodiments of the systems and methods described in the present disclosure is shown. As shown in FIG. 7, in some embodiments, computing device 650 can include a processor 702, a display 704, one or more inputs 706, one or more communication systems 708, and/or memory 710. In some embodiments, processor 702 can be any suitable hardware processor or combination of processors, such as a central processing unit ("CPU"), a graphics processing unit ("GPU"), and so on. In some embodiments, display 704 can include any suitable display devices, such as a computer monitor, a touchscreen, a television, and so on. In some embodiments, inputs 706 can include any suitable input devices and/or sensors that can be used to receive user input, such as a keyboard, a mouse, a touchscreen, a microphone, and so on.

In some embodiments, communications systems 708 can include any suitable hardware, firmware, and/or software for communicating information over communication network 654 and/or any other suitable communication networks. For example, communications systems 708 can include one or more transceivers, one or more communication chips and/or chip sets, and so on. In a more particular example, communications systems 708 can include hardware, firmware and/or software that can be used to establish a Wi-Fi connection, a Bluetooth connection, a cellular connection, an Ethernet connection, and so on.

In some embodiments, memory 710 can include any suitable storage device or devices that can be used to store instructions, values, data, or the like, that can be used, for example, by processor 702 to present content using display 704, to communicate with server 652 via communications system(s) 708, and so on. Memory 710 can include any suitable volatile memory, non-volatile memory, storage, or any suitable combination thereof. For example, memory 710 can include RAM, ROM, EEPROM, one or more flash drives, one or more hard disks, one or more solid state drives, one or more optical drives, and so on. In some embodiments, memory 710 can have encoded thereon, or otherwise stored therein, a computer program for controlling operation of computing device 650. In such embodiments, processor 702 can execute at least a portion of the computer program to present content (e.g., images, user interfaces, graphics, tables), receive content from server 652, transmit information to server 652, and so on.

In some embodiments, server 652 can include a processor 712, a display 714, one or more inputs 716, one or more communications systems 718, and/or memory 720. In some embodiments, processor 712 can be any suitable hardware processor or combination of processors, such as a CPU, a GPU, and so on. In some embodiments, display 714 can include any suitable display devices, such as a computer monitor, a touchscreen, a television, and so on. In some embodiments, inputs 716 can include any suitable input devices and/or sensors that can be used to receive user input, such as a keyboard, a mouse, a touchscreen, a microphone, and so on.

In some embodiments, communications systems 718 can include any suitable hardware, firmware, and/or software for communicating information over communication network 654 and/or any other suitable communication networks. For example, communications systems 718 can include one or more transceivers, one or more communication chips and/or chip sets, and so on. In a more particular example, communications systems 718 can include hardware, firmware and/or software that can be used to establish a Wi-Fi connection, a Bluetooth connection, a cellular connection, an Ethernet connection, and so on.

In some embodiments, memory 720 can include any suitable storage device or devices that can be used to store instructions, values, data, or the like, that can be used, for example, by processor 712 to present content using display 714, to communicate with one or more computing devices 650, and so on. Memory 720 can include any suitable volatile memory, non-volatile memory, storage, or any suitable combination thereof. For example, memory 720 can include RAM, ROM, EEPROM, one or more flash drives, one or more hard disks, one or more solid state drives, one or more optical drives, and so on. In some embodiments, memory 720 can have encoded thereon a server program for controlling operation of server 652. In such embodiments, processor 712 can execute at least a portion of the server program to transmit information and/or content (e.g., data, images, a user interface) to one or more computing devices 650, receive information and/or content from one or more computing devices 650, receive instructions from one or more devices (e.g., a personal computer, a laptop computer, a tablet computer, a smartphone), and so on.

In some embodiments, image source 602 can include a processor 722, one or more image acquisition systems 724, one or more communications systems 726, and/or memory 728. In some embodiments, processor 722 can be any suitable hardware processor or combination of processors, such as a CPU, a GPU, and so on. In some embodiments, the one or more image acquisition systems 724 are generally configured to acquire data, images, or both, and can include an MRI system. Additionally or alternatively, in some embodiments, one or more image acquisition systems 724 can include any suitable hardware, firmware, and/or software for coupling to and/or controlling operations of an MRI system. In some embodiments, one or more portions of the one or more image acquisition systems 724 can be removable and/or replaceable.

Note that, although not shown, image source 602 can include any suitable inputs and/or outputs. For example, image source 602 can include input devices and/or sensors that can be used to receive user input, such as a keyboard, a mouse, a touchscreen, a microphone, a trackpad, a trackball, and so on. As another example, image source 602 can include any suitable display devices, such as a computer monitor, a touchscreen, a television, etc., one or more speakers, and so on.

In some embodiments, communications systems 726 can include any suitable hardware, firmware, and/or software for communicating information to computing device 650 (and, in some embodiments, over communication network 654 and/or any other suitable communication networks). For example, communications systems 726 can include one or more transceivers, one or more communication chips and/or chip sets, and so on. In a more particular example, communications systems 726 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 728 can include any suitable storage device or devices that can be used to store instructions, values, data, or the like, that can be used, for example, by processor 722 to control the one or more image acquisition systems 724, and/or receive data from the one or more image acquisition systems 724; to images from data; present content (e.g., images, a user interface) using a display; communicate with one or more computing devices 650; and so on. Memory 728 can include any suitable volatile memory, non-volatile memory, storage, or any suitable combination thereof. For example, memory 728 can include RAM, ROM, EEPROM, one or more flash drives, one or more hard disks, one or more solid state drives, one or more optical drives, and so on. In some embodiments, memory 728 can have encoded thereon, or otherwise stored therein, a program for controlling operation of image source 602. In such embodiments, processor 722 can execute at least a portion of the program to generate images, transmit information and/or content (e.g., data, images) to one or more computing devices 650, receive information and/or content from one or more computing devices 650, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

Figure 8:
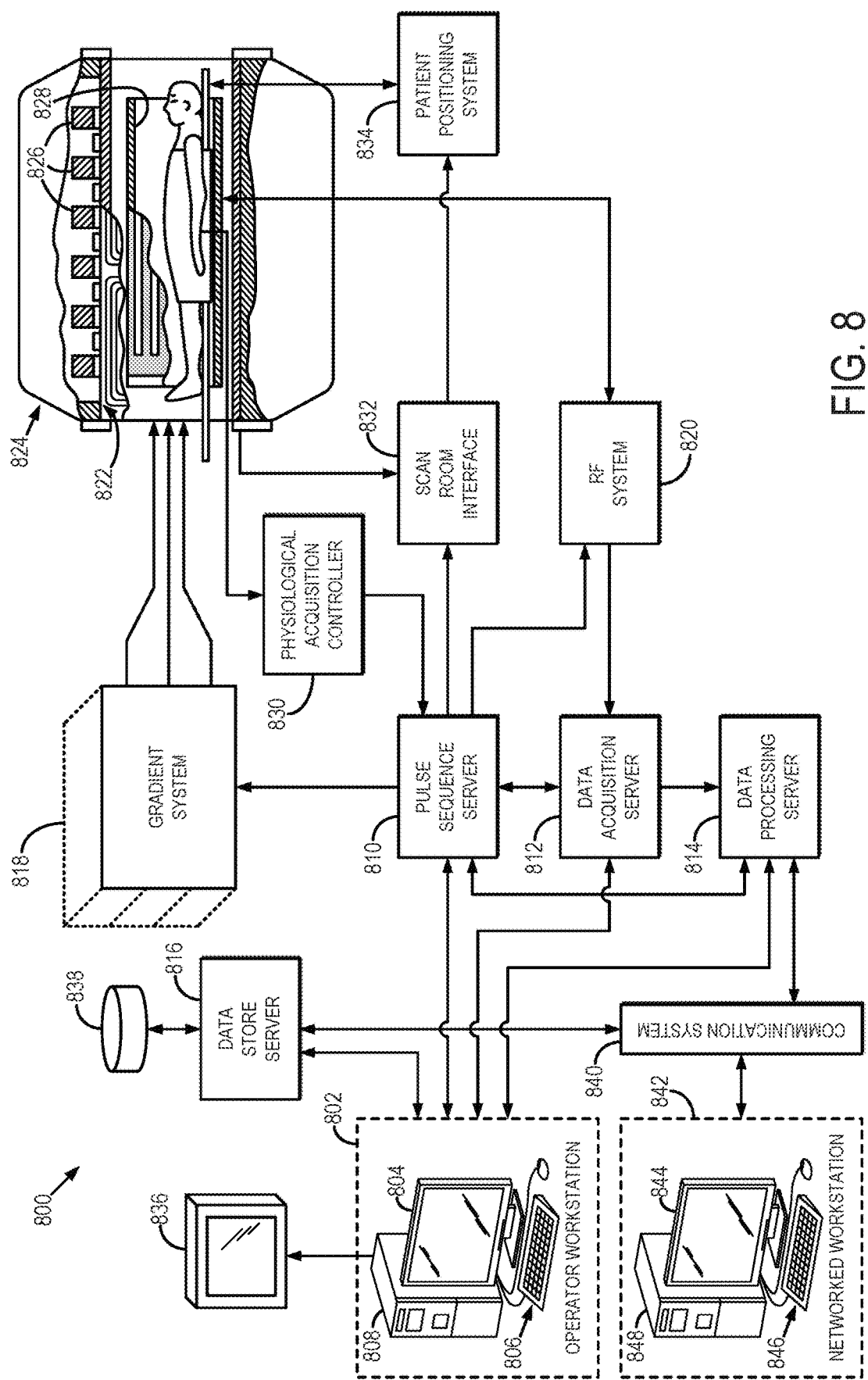
FIG. 8 is a block diagram of an MRI system that can implement the methods described in the present disclosure.

Referring particularly now to FIG. 8, an example of an MRI system 800 that can implement the methods described here is illustrated. The MRI system 800 includes an operator workstation 802 that may include a display 804, one or more input devices 806 (e.g., a keyboard, a mouse), and a processor 808. The processor 808 may include a commercially available programmable machine running a commercially available operating system. The operator workstation 802 provides an operator interface that facilitates entering scan parameters into the MRI system 800. The operator workstation 802 may be coupled to different servers, including, for example, a pulse sequence server 810, a data acquisition server 812, a data processing server 814, and a data store server 816. The operator workstation 802 and the servers 810, 812, 814, and 816 may be connected via a communication system 840, which may include wired or wireless network connections.

The pulse sequence server 810 functions in response to instructions provided by the operator workstation 802 to operate a gradient system 818 and a radiofrequency ("RF") system 820. Gradient waveforms for performing a prescribed scan are produced and applied to the gradient system 818, which then excites gradient coils in an assembly 822 to produce the magnetic field gradients $G_x$, $G_y$, and $G_z$ that are used for spatially encoding magnetic resonance signals. The gradient coil assembly 822 forms part of a magnet assembly 824 that includes a polarizing magnet 826 and a whole-body RF coil 828.

RF waveforms are applied by the RF system 820 to the RF coil 828, or a separate local coil to perform the prescribed magnetic resonance pulse sequence. Responsive magnetic resonance signals detected by the RF coil 828, or a separate local coil, are received by the RF system 820. The responsive magnetic resonance signals may be amplified, demodulated, filtered, and digitized under direction of commands produced by the pulse sequence server 810. The RF system 820 includes an RF transmitter for producing a wide variety of RF pulses used in MRI pulse sequences. The RF transmitter is responsive to the prescribed scan and direction from the pulse sequence server 810 to produce RF pulses of the desired frequency, phase, and pulse amplitude waveform. The generated RF pulses may be applied to the whole-body RF coil 828 or to one or more local coils or coil arrays.

The RF system 820 also includes one or more RF receiver channels. An RF receiver channel includes an RF preamplifier that amplifies the magnetic resonance signal received by the coil 828 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M = \sqrt{I^2 + Q^2} \quad (1)$$

and the phase of the received magnetic resonance signal may also be determined according to the following relationship:

$$\varphi = \tan^{-1}\left(\frac{Q}{I}\right). \quad (2)$$

The pulse sequence server 810 may receive patient data from a physiological acquisition controller 830. By way of example, the physiological acquisition controller 830 may receive signals from a number of different sensors connected to the patient, including electrocardiograph ("ECG") signals from electrodes, or respiratory signals from a respiratory bellows or other respiratory monitoring devices. These signals may be used by the pulse sequence server 810 to synchronize, or "gate," the performance of the scan with the subject's heart beat or respiration.

The pulse sequence server 810 may also connect to a scan room interface circuit 832 that receives signals from various sensors associated with the condition of the patient and the magnet system. Through the scan room interface circuit 832, a patient positioning system 834 can receive commands to move the patient to desired positions during the scan.

The digitized magnetic resonance signal samples produced by the RF system 820 are received by the data acquisition server 812. The data acquisition server 812 operates in response to instructions downloaded from the operator workstation 802 to receive the real-time magnetic resonance data and provide buffer storage, so that data is not lost by data overrun. In some scans, the data acquisition server 812 passes the acquired magnetic resonance data to the data processor server 814. In scans that require information derived from acquired magnetic resonance data to control the further performance of the scan, the data acquisition server 812 may be programmed to produce such information and convey it to the pulse sequence server 810. For example, during pre-scans, magnetic resonance data may be acquired and used to calibrate the pulse sequence performed by the pulse sequence server 810. As another example, navigator signals may be acquired and used to adjust the operating parameters of the RF system 820 or the gradient system 818, or to control the view order in which k-space is sampled. In still another example, the data acquisition server 812 may also process magnetic resonance signals used to detect the arrival of a contrast agent in a magnetic resonance angiography ("MRA") scan. For example, the data acquisition server 812 may acquire magnetic resonance data and processes it in real-time to produce information that is used to control the scan.

The data processing server 814 receives magnetic resonance data from the data acquisition server 812 and processes the magnetic resonance data in accordance with instructions provided by the operator workstation 802. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 814 are conveyed back to the operator workstation 802 for storage. Real-time images may be stored in a data base memory cache, from which they may be output to operator display 802 or a display 836. Batch mode images or selected real time images may be stored in a host database on disc storage 838. When such images have been reconstructed and transferred to storage, the data processing server 814 may notify the data store server 816 on the operator workstation 802. The operator workstation 802 may be used by an operator to archive the images, produce films, or send the images via a network to other facilities.

The MRI system 800 may also include one or more networked workstations 842. For example, a networked workstation 842 may include a display 844, one or more input devices 846 (e.g., a keyboard, a mouse), and a processor 848. The networked workstation 842 may be located within the same facility as the operator workstation 802, or in a different facility, such as a different healthcare institution or clinic.

The networked workstation 842 may gain remote access to the data processing server 814 or data store server 816 via the communication system 840. Accordingly, multiple networked workstations 842 may have access to the data processing server 814 and the data store server 816. In this manner, magnetic resonance data, reconstructed images, or other data may be exchanged between the data processing server 814 or the data store server 816 and the networked workstations 842, such that the data or images may be remotely processed by a networked workstation 842.

The present disclosure has described one or more preferred embodiments, and it should be appreciated that many equivalents, alternatives, variations, and modifications, aside from those expressly stated, are possible and within the scope of the invention.

The invention claimed is:

1. A method for generating a feature map that depicts a spatial distribution or pattern of a feature associated with osteolysis or synovitis, the steps of the method comprising:
    (a) accessing with a computer system, magnetic resonance imaging (MRI) data acquired from a subject;
    (b) accessing with the computer system, a trained machine learning algorithm that has been trained on training data to generate feature maps associated with synovitis;
    (c) inputting the MRI data to the trained machine learning algorithm in order to generate output with the computer system, wherein the output comprises at least one feature map that depicts a spatial distribution of a feature associated with synovitis, wherein the at least one feature map depicts the spatial distribution of a classification of locations within the subject as being associated with a type of synovitis at those locations.

2. The method as recited in claim 1, wherein the MRI data include segmented MRI data in which regions associated with synovial anatomy have been segmented.

3. The method as recited in claim 2, wherein the segmented MRI data are generated by inputting magnetic resonance images in the MRI data to a trained machine learning algorithm that has been trained on training data to generate segmented MRI data in which regions associated with synovial anatomy have been segmented.

4. The method as recited in claim 1, wherein step (c) further comprises generating at least one additional feature map that depicts the spatial distribution of a probability of locations within the subject being associated with at least one of osteolysis or synovitis.

5. The method as recited in claim 1, wherein step (c) comprises generating at least one additional feature map that depicts the spatial distribution of a classification of locations within the subject as being associated with a severity of synovitis at those locations.

6. The method as recited in claim 1, wherein step (b) includes generating the trained machine learning algorithm by:
    accessing training MRI data acquired from a plurality of subjects;
    generating segmented MRI data from the training MRI data, the segmented MRI data indicating regions associated with synovial anatomy in the plurality of subjects;
    assembling the training MRI data and the segmented MRI data with the computer system to generate training data;
    training a machine learning algorithm on the assembled training data.

7. The method as recited in claim 6, wherein the machine learning algorithm implements a neural network architecture.

8. The method as recited in claim 7, wherein the neural network architecture is an encoder-decoder neural network architecture.

9. The method as recited in claim 8, wherein inputting the MRI data to the trained machine learning algorithm comprises passing the MRI data to an encoding path of the encoder-decoder neural network, generating output; and passing the output from the encoding path of the encoder-decoder neural network to a decoding path of the encoder-decoder neural network, generating the feature map.

10. The method as recited in claim 9, wherein passing the MRI data to an encoding path of the encoder-decoder neural network includes:
    (i) passing MRI data to a convolutional layer, generating output;
    (ii) passing the output from the convolutional layer to a batch normalization layer, generating output;
    (iii) passing the output from the batch normalization layer to a nonlinear layer, generating output; and
    (iv) passing the output from the nonlinear layer to a downsampling layer, generating output.

11. The method as recited in claim 10, wherein passing the output of the encoding path of the encoder-decoder neural network to the decoding path of the encoder-decoder neural network includes:
    (i) passing the output of the encoding path of the encoder-decoder neural network to a transposed convolutional layer, generating output;
    (ii) passing the output from the transposed convolutional layer to a convolutional layer, generating output;
    (iii) passing the output from the convolutional layer to a batch normalization layer, generating output; and
    (iv) passing the output from the batch normalization layer to a nonlinear layer, generating output.

12. The method as recited in claim 1, wherein the MRI data comprise at least one of data or images acquired with an MRI system using multi-spectral imaging.

13. A method for constructing and implementing a machine learning algorithm to generate a feature map that depicts spatial patterns of a feature associated with synovitis across a region in a subject, the steps of the method comprising:
    constructing a trained machine learning algorithm by:
    (i) accessing training data with a computer system, the training data comprising magnetic resonance imaging (MRI) data acquired from a plurality of subjects and labeled data indicating a feature associated with synovitis for each of the plurality of subjects;
    (ii) training a machine learning algorithm based on the training data, wherein the machine learning algorithm is trained on the training data to generate a feature map indicating a spatial pattern of the feature across a region-of-interest; and
    generating a feature map that depicts a spatial pattern of the feature associated with synovitis by inputting magnetic resonance images acquired from the subject to the trained machine learning algorithm, wherein the feature associated with synovitis comprises a type of synovial reaction causing synovitis.

14. The method as recited in claim 13, wherein the training data further comprise segmented MRI data in which regions associated with synovial anatomy have been segmented.

15. The method as recited in claim 14, wherein the segmented MRI data are generated by inputting magnetic resonance images in the MRI data to a trained machine learning algorithm that has been trained on training data to generate segmented MRI data in which regions associated with synovial anatomy have been segmented.

16. The method as recited in claim 13, wherein the machine learning algorithm implements a neural network architecture.

17. The method as recited in claim 16, wherein the neural network architecture is an encoder-decoder neural network architecture.

18. A method for generating feature data that indicates a thickness of a synovial membrane in a subject, the steps of the method comprising:
   (a) accessing with a computer system, magnetic resonance imaging (MRI) data acquired from a subject;
   (b) accessing with the computer system, a trained machine learning algorithm that has been trained on training data to generate feature data that indicates a thickness of a synovial membrane;
   (c) inputting the MRI data to the trained machine learning algorithm in order to generate output with the computer system, wherein the output comprises feature data that indicates a thickness of a synovial membrane in the subject.

19. The method as recited in claim 18, wherein the trained machine learning algorithm implements an encoder-decoder neural network architecture having at least an encoding path, and wherein the feature data are generated as output of the encoding path of the encoder-decoder neural network.

\* \* \* \* \*